(12) United States Patent
Beeckler et al.

(10) Patent No.: US 11,878,095 B2
(45) Date of Patent: *Jan. 23, 2024

(54) BALLOON CATHETER WITH HIGH ARTICULATION

(71) Applicant: BIOSENSE WEBSTER (ISRAEL) LTD., Yokneam (IL)

(72) Inventors: Christopher Thomas Beeckler, Brea, CA (US); Joseph Thomas Keyes, Sierra Madre, CA (US); Kevin Justin Herrera, West Covina, CA (US); Alexander David Squires, Duarte, CA (US); Kevin Mark Okarski, Monrovia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 176 days.

This patent is subject to a terminal disclaimer.

(21) Appl. No.: 17/350,101

(22) Filed: Jun. 17, 2021

(65) Prior Publication Data

US 2021/0308424 A1 Oct. 7, 2021

Related U.S. Application Data

(63) Continuation of application No. 16/216,686, filed on Dec. 11, 2018, now Pat. No. 11,045,628.

(51) Int. Cl.
*A61M 25/01* (2006.01)
*A61M 25/00* (2006.01)
*A61M 25/10* (2013.01)

(52) U.S. Cl.
CPC ...... *A61M 25/0147* (2013.01); *A61M 25/005* (2013.01); *A61M 25/0136* (2013.01);
(Continued)

(58) Field of Classification Search
CPC .......... A61M 25/0147; A61M 25/0136; A61M 25/1002; A61M 25/1018; A61M 25/104;
(Continued)

(56) References Cited

U.S. PATENT DOCUMENTS

| 4,276,874 A | 7/1981 | Wolvek et al. |
| 4,699,147 A | 10/1987 | Chilson et al. |

(Continued)

FOREIGN PATENT DOCUMENTS

| CN | 111248993 A | 6/2020 |
| CN | 111248996 A | 6/2020 |

(Continued)

OTHER PUBLICATIONS

International Search Report and Written Opinion issued in corresponding International Patent Application No. PCT/B2019/060132 dated Mar. 19, 2020.

(Continued)

*Primary Examiner* — Darwin P Erezo
*Assistant Examiner* — Brigid K Byrd
(74) *Attorney, Agent, or Firm* — Troutman Pepper Hamilton Sanders LLP

(57) ABSTRACT

A medical probe includes a shaft, an expandable membrane and a probe maneuvering assembly (PMA). The shaft is configured for insertion into a cavity of an organ of a patient. The PMA is located inside the expandable membrane and includes a first elastic element, which is fitted along a longitudinal axis of the PMA and is configured to expand the membrane by shortening the PMA, and to collapse the membrane by elongating the PMA. The PMA further includes a second elastic element, which surrounds at least a portion of the first elastic element and is configured to deflect the membrane relative to the longitudinal axis.

20 Claims, 3 Drawing Sheets

(52) U.S. Cl.
CPC .... *A61M 25/1002* (2013.01); *A61M 25/1018* (2013.01); *A61M 25/104* (2013.01)

(58) Field of Classification Search
CPC ................ A61M 25/005; A61M 29/00; A61M 2025/1068; A61M 25/10
See application file for complete search history.

(56) References Cited

U.S. PATENT DOCUMENTS

| | | | |
|---|---|---|---|
| 4,734,093 A * | 3/1988 | Bonello | A61M 25/0147 604/95.04 |
| 4,940,064 A | 7/1990 | Desai | |
| 5,207,229 A | 5/1993 | Winters | |
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,395,327 A | 3/1995 | Undquist | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,766,192 A | 6/1998 | Zacca | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,590 A | 1/2000 | Whayne et al. | |
| 6,119,030 A | 9/2000 | Morency | |
| 6,142,993 A | 11/2000 | Whayne et al. | |
| 6,216,043 B1 | 4/2001 | Swanson et al. | |
| 6,216,044 B1 | 4/2001 | Kordis | |
| 6,321,749 B1 * | 11/2001 | Toti | A61M 16/04 128/207.14 |
| 6,428,537 B1 | 8/2002 | Swanson et al. | |
| 6,456,864 B1 | 9/2002 | Swanson et al. | |
| 6,574,492 B1 | 6/2003 | Ben-Haim et al. | |
| 6,584,345 B2 | 6/2003 | Govari | |
| 6,585,717 B1 | 7/2003 | Wittenberger et al. | |
| 6,600,948 B2 | 7/2003 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| RE41,334 E | 5/2010 | Beatty et al. | |
| 7,846,157 B2 | 12/2010 | Kozel | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,936,612 B2 * | 1/2015 | Suehara | A61B 1/0057 606/192 |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |

(56) References Cited

U.S. PATENT DOCUMENTS

| | | |
|---|---|---|
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2004/0193032 A1 | 9/2004 | Mogul |
| 2004/0210121 A1 | 10/2004 | Fuimaono et al. |
| 2005/0055048 A1 | 3/2005 | Dieck et al. |
| 2006/0009689 A1 | 1/2006 | Fuimaono et al. |
| 2006/0009690 A1 | 1/2006 | Fuimaono et al. |
| 2006/0064058 A1* | 3/2006 | Coyle ............... A61M 25/0147 604/103.04 |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2009/0312807 A1 | 12/2009 | Boudreault et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0116382 A1 | 5/2012 | Ku et al. |
| 2012/0143130 A1 | 6/2012 | Subrananiam et al. |
| 2013/0090651 A1 | 4/2013 | Smith |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0112255 A1 | 4/2015 | Jensen et al. |
| 2015/0119878 A1 | 4/2015 | Heisel et al. |
| 2015/0133760 A1 | 5/2015 | Kordis et al. |
| 2015/0133860 A1 | 5/2015 | Kordis et al. |
| 2015/0133919 A1 | 5/2015 | McDaniel et al. |
| 2015/0173772 A1 | 6/2015 | Bowman et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |

(56) References Cited

U.S. PATENT DOCUMENTS

| | | |
|---|---|---|
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| JP | S55106168 A | 8/1980 |
| JP | 2002360704 A | 12/2002 |
| JP | 2007503914 A | 3/2007 |
| JP | 2008513111 A | 5/2008 |
| JP | 2014502180 A | 1/2014 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |

(56) References Cited

FOREIGN PATENT DOCUMENTS

| | | |
|---|---|---|
| WO | 2019084442 A1 | 5/2019 |
| WO | 2019143960 A1 | 7/2019 |
| WO | 2020026217 A1 | 2/2020 |
| WO | 2020206328 A1 | 10/2020 |

OTHER PUBLICATIONS

International Preliminary Report on Patentability for International Application No. PCT/IB2019/060132, dated Jun. 24, 2021, 9 Pages.
International Search Report and Written Opinion for International Application No. PCT/IB2019/060132, dated Mar. 19, 2020, 12 Pages.
Notice of Reasons for Refusal dated Aug. 22, 2023, from Corresponding Japanese Application No. 2021-533211.
Search Report dated Aug. 25, 2023, from Corresponding Japanese Application No. 2021-533211.

\* cited by examiner

BALLOON CATHETER WITH HIGH ARTICULATION

CROSS-REFERENCE TO RELATED APPLICATION

This application is a continuation of prior filed U.S. patent application Ser. No. 16/216,686 filed on Dec. 11, 2018 which is hereby incorporated by reference as set forth in full herein.

FIELD

The present invention relates generally to medical probes, and particularly to balloon catheters.

BACKGROUND

Various catheters employ steering mechanisms so as to maneuver their distal end. For example, U.S. Patent Application Publication 2015/0173772 describes a catheter system utilizing one or more sensors. The catheter can be used as part of an embolic coil system, guidewire system, or combined embolic coil/guidewire system where the devices interact with the catheter system. A variable detachment embolic coil system and guidewire system are also described, wherein part of a device is detached to leave an implant behind.

As another example, U.S. Patent Application Publication 2004/0193032 describes a diagnostic catheter with a steering device to direct the distal end of the catheter while it is inserted in a vessel. The catheter may include either a bi-directional steering mechanism, or a unidirectional steering mechanism. The catheter may be embodied as a basket catheter including a plurality of splines. A central retractable and steerable member is included to provide the expansion force. The expansion force can also be provided by moving the proximal portion of the catheter relative to the central member. Each of the splines forming the basket includes a length of spring wire disposed therein to provide conformal forces causing the splines to conform to the surfaces being inspected.

U.S. Pat. No. 6,585,717 describes deflection mechanisms that are positioned so as to deflect portions of a flexible body, such as a catheter, in more than one direction in a single plane, as well as in more than one plane. The invention allows a distal portion of a catheter to be deflected more than 360 degrees to provide a loop. In an embodiment, a deflection structure of the catheter may be made of polymer, a spring-tempered stainless or super-elastic alloy that when released from a sheath will force the catheter tip to take a shape desired. Tension may be applied to a pull-wire, thereby causing the deflection structure to bend.

U.S. Pat. No. 5,395,327 describes a steering mechanism including a steering shaft coupled to a controller which includes a handle and apparatus for manipulating the distal end of the steering shaft. The steering shaft includes a flexible coiled spring having a lead spring fixed in position with respect to a distal end thereof in the distal end of the steering shaft. Steering wires are affixed at the distal ends thereof to the lead spring. The steering wires extend through the steering shaft to the controller, and the steering apparatus of the controller is used to place tension on the steering wires. The attachment of the distal ends of the steering wires to the lead spring may be opposite one another or may be offset for providing greater maneuverability. Tension may be placed on the steering wires by wedges mounted transversely to the controller housing, or by rotation of a shaft mounted transversely to the controller housing, the steering wires being attached to the shaft such that rotation in one direction tenses one steering wire, and rotation in the other direction tenses the other steering wire. Two independently rotatable shafts may be used to separately control the two steering wires.

SUMMARY

Deflecting a balloon catheter is challenging, particularly if the balloon needs to be maneuvered within the left atrium. The balloon catheter is normally fed (over a guidewire) into the left atrium in a deflated state via a sheath, and it is then inflated or expanded. For correct positioning prior to an ablation, the balloon needs to be inflated or expanded and deflected to the desired location within the heart. However, upon exiting catheter sheath, the relatively small size of the left atrium limits the freedom of movement for deflection of the balloon. Recognizing this, the inventor has devised an invention for the balloon with a mechanism that allows for inflation of the balloon as well as deflection of the balloon, and the two operations can be performed independently.

In particular, an embodiment of the present invention provides a medical probe including a shaft, an expandable membrane and a probe maneuvering assembly (PMA). The shaft is configured for insertion into a cavity of an organ of a patient. The PMA is located inside the expandable membrane and includes a first elastic element, which is fitted along a longitudinal axis of the PMA and is configured to expand the membrane by shortening the PMA, and to collapse the membrane by elongating the PMA. The PMA further includes a second elastic element, which surrounds at least a portion of the first elastic element and is configured to deflect the membrane relative to the longitudinal axis.

In some embodiments, a length of the second elastic element is configured to determine a bending-location over the PMA.

In some embodiments, the medical probe further includes a hollow tube, which runs inside the shaft, wherein a distal edge of the hollow tube is coupled to a distal end of the PMA, for shortening or elongating the PMA.

In some embodiments, the medical probe further includes one or more puller wires, which are connected to the second elastic element for deflecting the membrane.

In an embodiment, the one or more puller wires each comprises a yarn.

In another embodiment, the yarn is made of Ultra High Molecular Weight Polyethylene (UHMWPE) material.

In some embodiments, the medical probe further includes a catheter handle, which includes a ratcheting mechanism configured to rotate so as to control an amount of tension on the one or more puller wires.

In an embodiment, the catheter handle includes a rocker configured to deflect the PMA using the one or more puller wires, wherein a center of the rocker has an opening for passing the hollow tube.

In some embodiments, the first and second elastic elements comprise respective first and second springs.

In an embodiment, the first and second springs are helical, wherein the first spring has a first handedness, and wherein the second spring has a second handedness that is opposite to the first handedness.

In some embodiments, the second elastic element is a flexible tube.

In some embodiments, the medical probe further includes a ring, which is slid over the flexible tube and is connected to the one or more puller wires.

In an embodiment, a portion of the flexible tube wraps a coupling member at a distal edge of the shaft, wherein the coupling member couples the PMA to the shaft.

In another embodiment, a proximal edge of the expandable membrane is coupled to the flexible tube.

There is additionally provided, in accordance with an embodiment of the present invention, a manufacturing method including mounting inside an expandable membrane a probe maneuvering assembly (PMA) that includes (a) a first elastic element, which is fitted along a longitudinal axis of the PMA and is configured to expand the membrane by shortening the PMA, and to collapse the membrane by elongating the PMA, and (b) a second elastic element, which surrounds at least a portion of the first elastic element and is configured to deflect the membrane relative to the longitudinal axis. The PMA and the membrane are connected at a distal edge of a shaft for insertion into a cavity of an organ of a patient using a coupling member.

There is additionally provided, in accordance with an embodiment of the present invention, a method including inserting, into a cavity of an organ of a patient, a probe including (a) a shaft, (b) an expandable membrane, and (c) a probe maneuvering assembly (PMA), which is located inside the expandable membrane, wherein the PMA includes (i) a first elastic element fitted along a longitudinal axis of the PMA, and (ii) a second elastic element surrounding at least a portion of the first spring. Using the first elastic element, the membrane is expanded by shortening the PMA, and the membrane is collapsed by elongating the PMA. The membrane is deflected relative to the longitudinal axis using the second elastic element.

The present invention will be more fully understood from the following detailed description of the embodiments thereof, taken together with the drawings in which:

DETAILED DESCRIPTION

Overview

Figure 1:
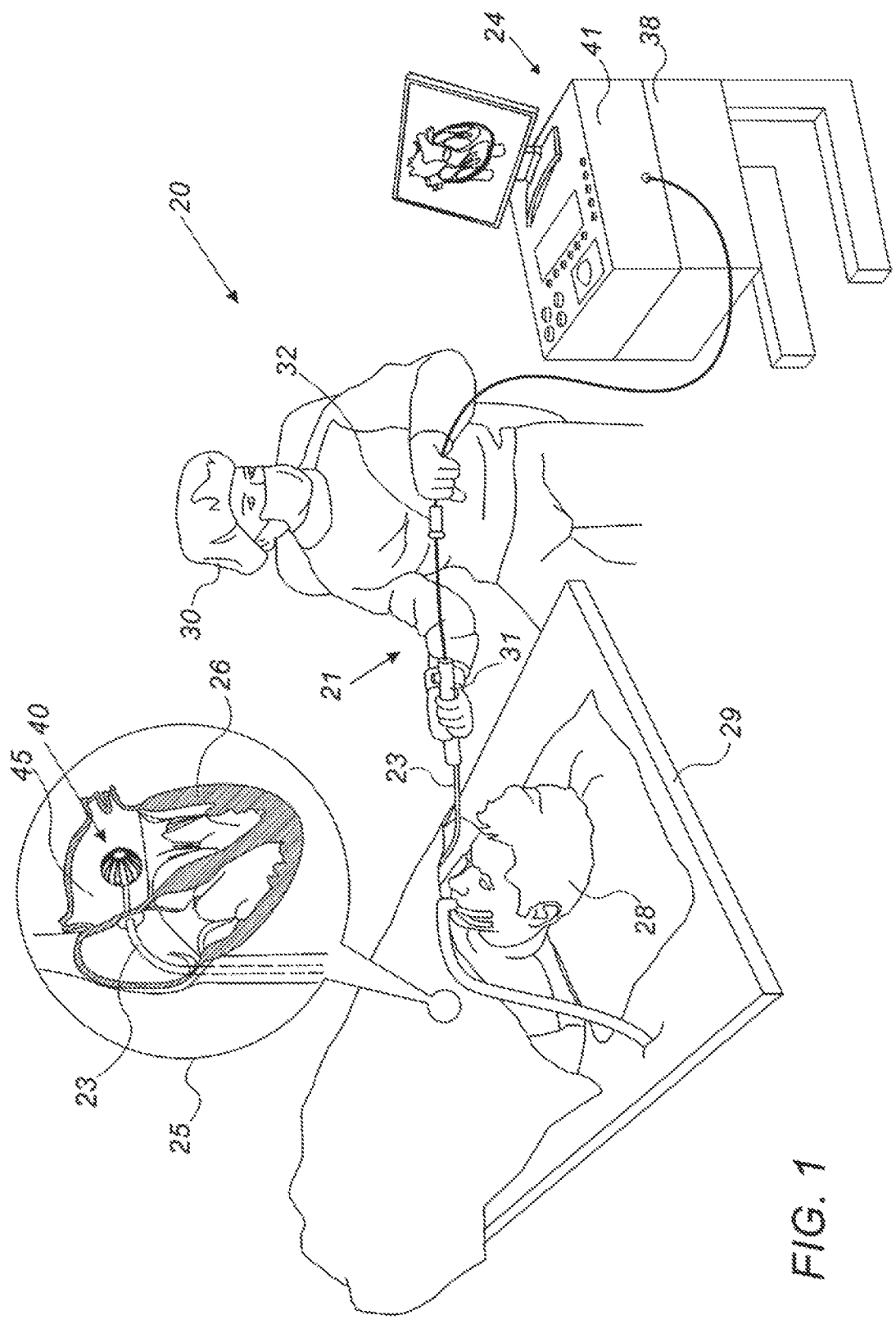
FIG. 1 is a schematic, pictorial illustration of a balloon catheterization system comprising a maneuverable balloon catheter, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

Embodiments of the present invention that are described hereinafter provide medical probes, such as expandable balloon catheters having a probe maneuvering assembly (PMA). The PMA enables to, independently and simultaneously, expand or collapse a balloon membrane, as well as deflect the balloon membrane, a mode of operation called "maneuvering the balloon" in the context of the disclosed description. The disclosed embodiments of a PMA thus increase the freedom of movement to, for example, deflect the balloon inside a small-size cavity of a patient's organ, such as inside the left atrium of a heart.

In some embodiments, a shaft including a hollow tube for insertion into the cavity is provided, wherein the hollow tube runs inside the hollow shaft. The PMA, which is coupled at its proximal edge to the distal edge of the shaft using a coupling member, is further coupled, at a nose piece included in a distal edge of the PMA, to the distal edge of the hollow tube (i.e., a distal edge of the hollow tube is coupled to a distal end of the PMA). The PMA further includes (a) a first elastic element, which is fitted along a longitudinal axis of the PMA and is configured to expand the membrane by shortening the PMA, and to collapse the membrane by elongating the PMA, and (b) a second elastic element, which surrounds at least a portion of the first elastic element and is configured to deflect the membrane relative to the longitudinal axis.

In some embodiments, the first and second elastic elements are springs. In other embodiments the PMA includes a flexible tube as the second elastic element instead of the second spring. Typically, the flexible tube is made of polymer material that can be extruded to form the tube. Other suitable types of elastic elements can also be used to implement the first and/or second elastic element.

The expandable membrane of a balloon surrounds the PMA with a distal edge of the expandable membrane coupled to the nose piece. A proximal edge of the expandable membrane is coupled to the distal edge of the shaft. The expandable membrane can be either expanded or collapsed when pulling or releasing the hollow tube, respectively, while, in parallel, it can be deflected by pulling one or more puller wires. In other words, the expandable membrane is either expanded or collapsed when the PMA is shortened or elongated, respectively, and is simultaneously deflected when the PMA is deflected.

In some embodiments, the second (outer) elastic element is shorter than the first (inner) elastic element in the distal direction. In this way, the outer elastic element does not constrain longitudinal motion (i.e., contraction or elongation) of the inner elastic element. The two elastic elements are nested, and the hollow tube nests within the inner elastic element, so as to minimize the overall diameter of the PMA. In some embodiments, in which the elastic elements are springs, the two springs may have opposite handedness so that helices of the two springs do not overlap.

In other embodiments, in which the second elastic element is a flexible tube, the flexible tube wraps the coupling member at a distal edge of the shaft and covers at least a proximal portion of the first elastic element. A metal ring is slid over the distal edge of the flexible tube, with the puller-wires coupled to the metal ring so as to deflect the flexible tube. The puller wires are inserted through dedicated channels (e.g., extrusions) along the wall of the flexible tube, as described below.

The above-described two embodied arrangements of the components of the PMA allows the deflection of the balloon closer to the geometrical center of the balloon. Therefore, the arc length of the deflection is smaller than the length of a typical left atrium, significantly increasing the utility of this type of maneuvering method.

In some embodiments, the puller wire is made from ultra-high molecular weight polyethylene (UHMWPE) yarn. The coupling of the yarn to the outer spring is resistant to sharp bending (i.e., deflection) of the outer spring, as the yarn does not require welding to the distal edge of the spring, which, as the spring bends, is a potential point of delamination of other types of puller wires. The UHMWPE yarn is terminated directly in the catheter handle, in a ratcheting mechanism that is integrated into the molded handle. The ratcheting mechanism allows the assembler to finely control, during manufacturing, the amount of slack on each yarn by rotating the ratchet mechanism.

The hollow tube is fixed, inside the handle, to a block which glides in a path defined by a rotating knob which provides the retraction necessary to pull the distally located nose piece backward, and to compress the inner spring, so as to shorten the PMA. Proximal to the rotating knob is the bidirectional rocker which provides bidirectional deflection of the balloon.

In an embodiment, the center of the rocker has an opening to allow the hollow tube to pass through without having to take a sharp bend, which is critical to reduce the insertion/retraction forces experienced by the hollow tube.

The hollow tube is configured to be retracted or relapsed from the handle of the catheter so as to expand or collapse the membrane. The puller wires are configured to be pulled or released from the handle in parallel to the motion of the hollow tube, so as to deflect the membrane in parallel (i.e., maneuvering the balloon together, as defined above).

In some embodiments, a related balloon treatment method is provided to enable maneuvering the balloon inside a cavity, so as to access target tissue with the expandable membrane. This additional balloon maneuvering establishes firm physical contact between the expanded membrane and target tissue, at which time the tissue is treated, for example, by applying radiofrequency ablation using electrodes disposed over the expandable membrane in physical contact with tissue.

The disclosed PMA, and the related balloon treatment method, gives a physician access to tissue with a balloon catheter that might otherwise be less accessible, or inaccessible, to balloon treatment limited to the simple maneuvers available to catheters without the disclosed PMA and PMA maneuvering method. Such maneuverability increases the chances of successful completion of a diagnostic and/or invasive therapeutic cardiac procedure, such as pulmonary vein isolation (PVI) from inside the left atrium for treatment of atrial fibrillation.

System Description

FIG. 1 is a schematic, pictorial illustration of a balloon catheterization system 20 comprising a maneuverable balloon catheter 40, in accordance with an embodiment of the present invention. System 20 comprises a catheter 21, wherein a coupling member is mounted to the distal edge of the shaft (shown in FIG. 2 below) of the catheter. Balloon catheter 40 is inserted by a physician 30 through a sheath 23 into a cavity 45 of heart 26, seen in inset 25, of a patient 28 lying on a table 29. To reach a target location inside cavity 45, shown to be a left atrium 45 of heart 26, physician 30 navigates the distal end of balloon catheter 40, by deflection from the sheath 23.

During the insertion of balloon catheter 40, balloon catheter 40 is maintained in a collapsed configuration by sheath 23. By containing balloon catheter 40 in a collapsed configuration, sheath 23 also serves to minimize vascular trauma along the way to the target location.

Physician 30 then maneuvers catheter 40 inside cavity 45 using catheter handle 31 so as to access and contact target tissue. In the process, physician 30 simultaneously and independently maneuvers balloon 44 that is fitted for these maneuvers with the disclosed PMA, as described below.

The proximal end of catheter 21 is connected to a control console 24. In the embodiment described herein, catheter 21 may be used for any suitable therapeutic and/or diagnostic purpose, such as electrical sensing, or balloon angioplasty and ablation of tissue in heart 26, among other possible medical usages of expandable balloon catheters.

Control console 24 comprises a processor 41, typically a general-purpose computer, with a suitable front end and interface circuits 38 for receiving signals from catheter 21, as well as for applying treatment via catheter 21 in heart 26 and for controlling the other components of system 20. Processor 41 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise other components and perform non-cardiac treatments.

Balloon Catheter with High Articulation

Figure 2A:
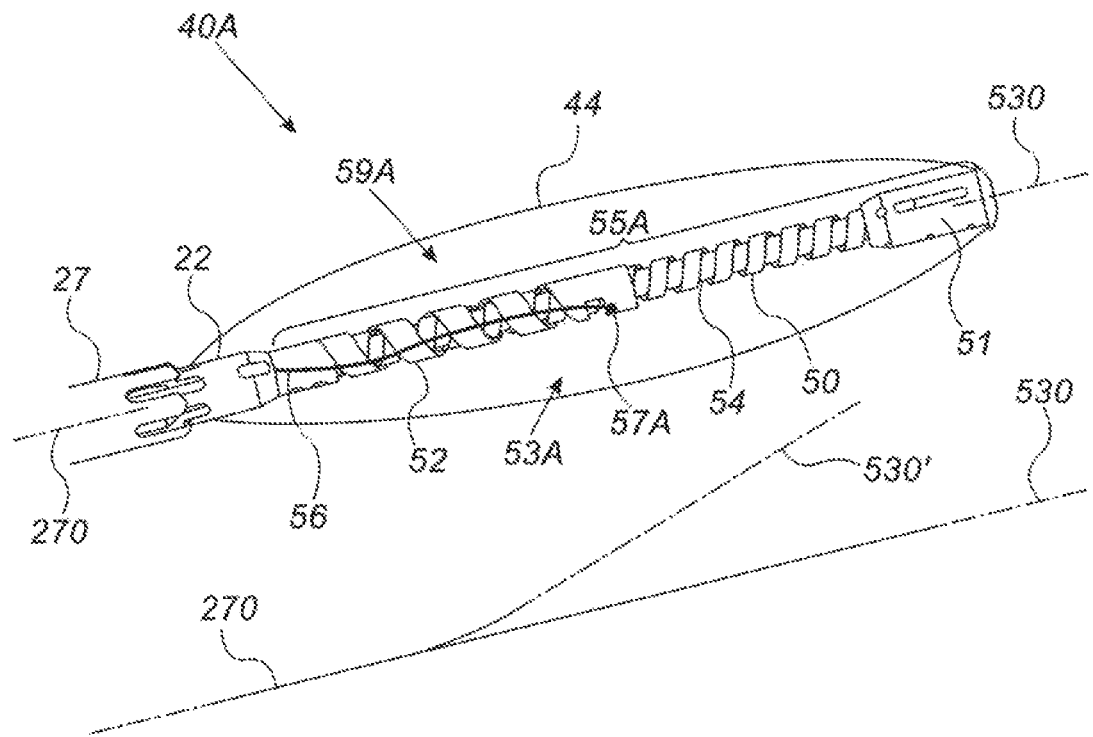
FIGS. 2A and 2B are schematic, detailed pictorial illustration of maneuverable balloon catheters, which comprise probe maneuvering assemblies (PMAs), in accordance with embodiments of the present invention.

FIG. 2A is a schematic, detailed pictorial illustration of a maneuverable balloon catheter 40A, which comprises a probe maneuvering assembly (PMA, also referred to herein as "balloon maneuvering assembly"), in accordance with an embodiment of the present invention. As seen in FIG. 2A catheter 40A further comprises an expandable membrane 44, which is seen in a collapsed state, and which is coupled at its proximal end to coupling member 22 and at its distal end to a nose 51 of PMA 55A.

The following description of FIG. 2A describes how PMA 55A is used to simultaneously and independently expand or collapse, as well as deflect, membrane 44 of balloon catheter 40.

As seen, PMA 55 comprises nose 51 and a concentric two-spring mechanism 53. A second (outer) spring 52 of concentric two-spring mechanism 53 is coupled at its proximal end to coupling member 22 and encompasses a portion of first (inner) spring 50 to form the concentric arrangement of the two springs (i.e., the aforementioned concentric two-spring mechanism 53).

Nose 51 is coupled to a distal edge of inner spring 50, and can be pulled proximally, or extended distally, by retracting or releasing a hollow tube 54, against the expanding force of inner spring 50, respectively. Therefore, membrane 44 can be expanded or collapsed by pulling or releasing tension, respectively, in hollow tube 54 from catheter handle 31.

In some embodiments, when hollow tube 54 is pulled to compress inner spring 50, membrane 44 expands into a spherical shape, a process which may be further assisted by flowing saline solution under pressure into the balloon, for example, through hollow tube 54. In some embodiments, hollow tube 54 is made of a thick-walled polyimide tube, which also serves as the lumen through which a thin guidewire can pass.

As seen, a puller wire 56 is attached to a distal end of second (outer) spring 52, at an anchoring point 57A. When pulled by a puller wire 56, outer spring 52 bends, causing PMA 55 to bend and to deflect expandable membrane 44 (i.e., deflect the balloon catheter). Typically, outer spring 52 is designed to be shorter and stiffer than inner spring 50. In an embodiment, the length of outer spring 52 is chosen so as to cause the bending of balloon maneuvering assembly 55 at a bending point 59A, at a given distance proximally to anchoring point 57A. Another puller wire (not shown) is coupled to outer spring 52 directly opposite to puller wire 56 to enable bi-directional deflection of balloon catheter 40.

In the context of this description, terms such as "deflection," "deflect" and "deflectable" refer to a situation in which a longitudinal axis 530 of the PMA is at some non-zero angle relative to a longitudinal axis 270 of shaft 27 (e.g., longitudinal axis 530 is pointing at a deflected direction 530' that is not parallel with the longitudinal axis).

In other embodiments, anchoring point 57A is located at a given location along outer spring 52 (along longitudinal axis 530 of the PMA), such as at approximately the center of outer spring 52. The more proximal puller wire anchoring point 57A the tighter the bend radius of outer spring 52, and stiffer and more difficult to deflect. An optimized location of point 57A would occur to a person skill in the art.

In an embodiment, to give a firm structure to PMA 55A, both springs 50 and 52 are sized to have minimal gaps between each other and hollow tube 54. To reduce friction, springs 50 and 52 are electropolished to round corners, and their handedness is reversed so as to prevent one helical cut to fall within the gap of the other spring, thus avoiding obstructing the maneuvering of balloon catheter 40.

Figure 2B:
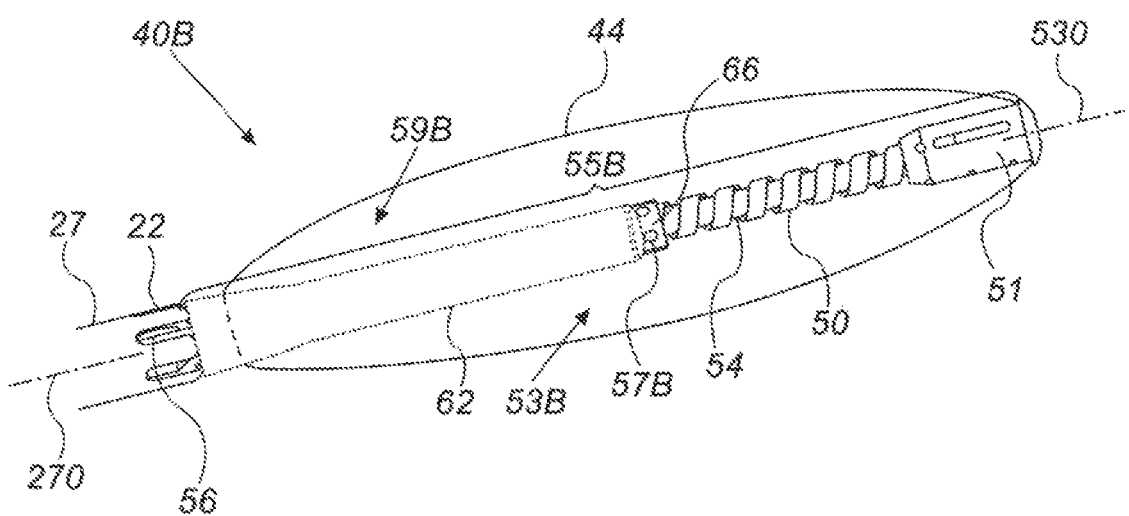

FIG. 2B is a schematic, detailed pictorial illustration of a maneuverable balloon catheter 40B, which comprises a PMA 55B, in accordance with an alternative embodiment of the present invention. As seen in FIG. 2B catheter 40B further comprises an expandable membrane 44, which is seen in a collapsed state, and which is coupled at its proximal end to a flexible tube 62 (instead of outer spring 52) that wraps a distal section of coupling member 22 and at its distal end to a nose 51 of PMA 55B.

FIG. 2B illustrates how PMA 55B is used to simultaneously and independently expand or collapse, as well as deflect, membrane 44 of balloon catheter 40. As seen, in PMA 55B comprises nose 51 and a concentric two-elastic-element mechanism 53B. In the shown embodiment, flexible tube 62 covers over spring 50 to define that (a) tube 62 is "concentric" to spring 50 and (b) that tube 62 and spring 50 make up the two-elastic-element. Flexible tube 62 of concentric two-elastic-element mechanism 53B is coupled at its proximal end to coupling member 22 and encompasses a portion of first (inner) spring 50 to form the concentric arrangement of the two elastic elements (i.e., the aforementioned concentric two-elastic-element mechanism 53B).

Nose 51 is coupled to a distal edge of inner spring 50, and can be pulled proximally, or extended distally, by retracting or releasing a hollow tube 54, against the expanding force of inner spring 50, respectively. Therefore, membrane 44 can be expanded or collapsed by pulling or releasing tension, respectively, in hollow tube 54 from catheter handle 31.

As seen, a puller wire 56 is attached to a ring 66 slid over the distal end of flexible tube 62, at an anchoring point 57B over ring 66. When pulled by a puller wire 56, flexible tube 62 bends, causing PMA 55 to bend and to deflect expandable membrane 44 (i.e., deflect the balloon catheter). Typically, flexible tube 62 is designed to be shorter and stiffer than inner spring 50. In an embodiment, the length of outer spring 52 is chosen so as to cause the bending of balloon maneuvering assembly 55 at a bending point 59B, at a given distance proximally to anchoring point 57B. Another puller wire (not shown) is coupled to ring 66 directly opposite to puller wire 56 to enable bi-directional deflection of balloon catheter 40B.

In an embodiment, to give a firm structure to PMA 55B, the wall of flexible tube 62 is braded with a mesh made of woven metal wires (not shown). The example illustrations shown in FIGS. 2A and 2B are chosen purely for the sake of conceptual clarity. Other mechanical solutions can be used in alternative embodiments. For example, another flexural component, such as a perforated flexible beam, may replace springs 50 and/or one of spring 52 and flexible tube 62.

Figure 3:
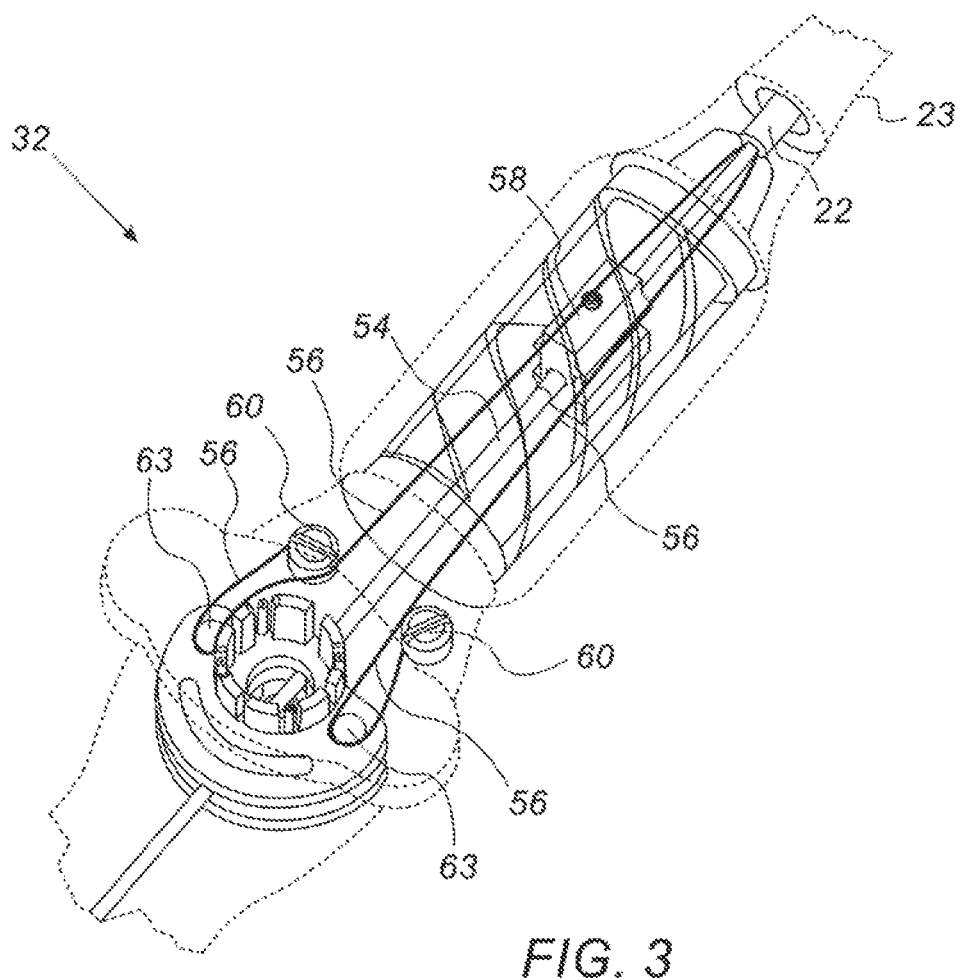
FIG. 3 is a schematic, pictorial illustration of the handle of the catheter of FIG. 1, which comprises two ratcheting mechanisms, in accordance with an embodiment of the present invention.

FIG. 3 is a schematic, pictorial illustration of catheter handle 31 of the catheter of FIG. 1, which comprises two ratcheting mechanisms 60, in accordance with an embodiment of the present invention. As seen, hollow tube 54, which comes from nose 51 of PMA 55, is bonded to a traveler 58. When traveler 58 is pulled back by a knob in handle 31 (i.e., by physician 30), hollow tube 54 pulls on nose 51 and compresses inner spring 50.

Two puller-wires 56 are implemented as UHMWPE yarns, alternatively Liquid Crystal Polymer, or any other suitable polymer may be used. Yarns 56 go into pulley assembly 63 that includes a rotating knob to bidirectionally deflect balloon catheter 40. Yarns 56 are then tethered to ratcheting mechanisms 60, which are integrated into the molded handle. Ratcheting mechanisms 60 allow, during manufacturing, fine control of the amount of slack on each yarn by rotating the ratchet mechanism by "one click" that equals a length of L/N, where L is the circumference of the ratchet, and N is the number of the ratchet teeth. As further seen, the center of pulley assembly 62 has an opening to allow hollow tube 54 to pass through without having to take a sharp bend, so as to reduce the insertion/retraction forces experienced by the hollow tube. Alternatively, puller wires may be made of stainless steel or any other suitable wire. The yarn may be attached to the ratchet and around the pulley and then secured to the wire.

The example illustration shown in FIG. 3 is chosen purely for the sake of conceptual clarity. Any other suitable configuration can be used in alternative embodiments, for example, a multiplicity of puller wires 56 may be used to enable multi-directional deflection of balloon 44.

Figure 4:
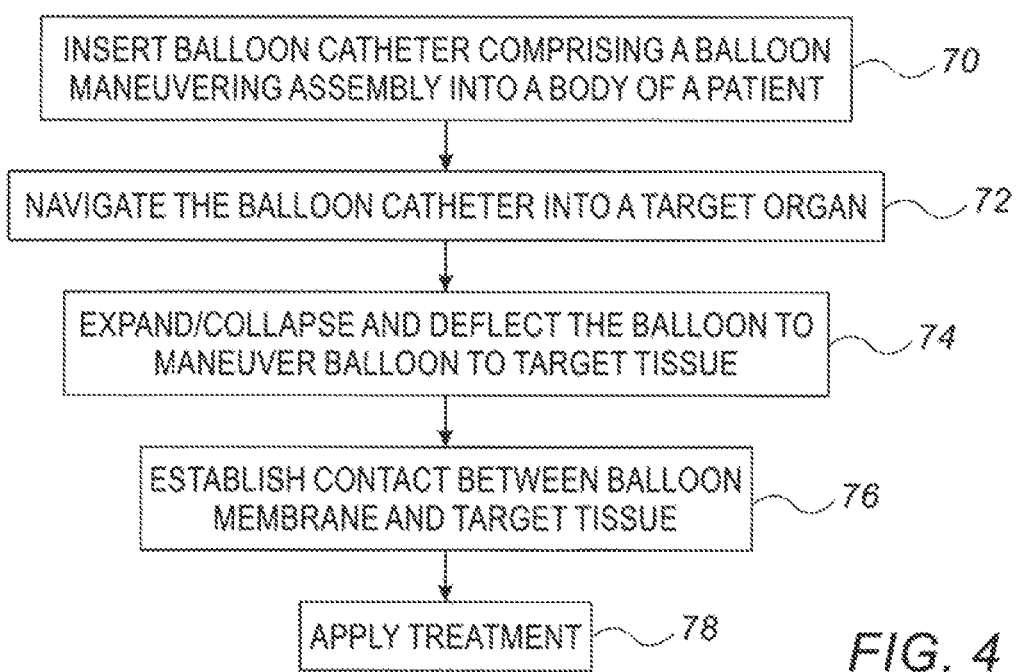
FIG. 4 is a flow chart that schematically illustrates a method of balloon treatment using a balloon equipped with the PMA of FIG. 2, in accordance with an embodiment of the present invention.

FIG. 4 is a flow chart that schematically illustrates a method of balloon treatment using a balloon equipped with PMA 55 of FIG. 2, in accordance with an embodiment of the present invention. A treatment begins with physician 30 inserting balloon catheter 40 into a body of a patient, at a balloon insertion step 70. Next, the physician navigates balloon catheter 40 into an organ, at a balloon navigation step 72. Next, at a balloon maneuvering step 74, using handle 31 to operate PMA 55, physician 30 maneuvers the balloon inside a small cavity, such as left atrium 45 of heart 26, so as to access target tissue with membrane 44. During step 74 membrane 44 might be partially expanded, and only at the end of the maneuvering process, will membrane 44 be fully expanded.

Physician 30 then further maneuvers the balloon using PMA 55, so as to establish firm contact between membrane 44 and target tissue, at a balloon contacting step 76. The physician next treats target tissue, at a balloon treatment step 78, for example by radiofrequency ablation using the electrodes disposed on membrane 44 that were maneuvered into contact with tissue.

The example flow chart shown in FIG. 4 is chosen purely for the sake of conceptual clarity. Additional steps, such the full expansion of the balloon, inflation the balloon with pressurized saline solution and the operation of irrigation, as well as collapsing and retracting the balloon, are omitted from the purposely highly simplified flow chart.

Although the embodiments described herein mainly address pulmonary vein isolation, the methods and systems described herein can also be used in other applications, such as in otolaryngology or neurology procedures.

It will thus be appreciated that the embodiments described above are cited by way of example, and that the present invention is not limited to what has been particularly shown and described herein above. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A medical probe, comprising:
   an elongated shaft defining a longitudinal axis;
   a probe maneuvering assembly (PMA) extending along the longitudinal axis at a distal end of the elongated shaft;
   a handle positioned at a proximal end of the elongated shaft, configured to change a length of the PMA, and configured to deflect the PMA from the longitudinal axis; and
   an expandable membrane comprising an internal volume including the PMA, configured such that the internal volume changes in response to changing the length of the PMA, and configured to deflect from the longitudinal axis in response to the PMA deflecting from the longitudinal axis.

2. The medical probe of claim 1, wherein the handle is configured to change the length of the PMA independent of deflecting the PMA from the longitudinal axis.

3. The medical probe of claim 1, wherein the PMA comprises:
   a first elastic element configured to increase the internal volume of the expandable membrane by foreshortening the PMA and configured to decrease the internal volume of the expandable membrane by elongating the PMA; and
   a second elastic element configured to deflect the PMA from the longitudinal axis, thereby deflecting the expandable membrane from the longitudinal axis.

4. The medical probe of claim 3, wherein the second elastic element surrounds at least a portion of the first elastic element.

5. The medical probe of claim 3, wherein the first elastic element comprises a first spring and wherein the second elastic element comprises a second spring.

6. The medical probe of claim 5, wherein the first and second springs are helical, wherein the first spring has a first handedness, and wherein the second spring has a second handedness that is opposite to the first handedness.

7. The medical probe of claim 3, wherein the second elastic element comprises a flexible tube.

8. The medical probe of claim 7, further comprising:
   a ring slid over the flexible tube; and
   a puller wire connected to the ring and configured to deflect the PMA.

9. The medical probe of claim 7, wherein a proximal edge of the expandable membrane is coupled to the flexible tube.

10. The medical probe of claim 3, further comprising:
    a first puller wire extending from the handle to the second elastic element; and
    a second puller wire extending from the handle to the second elastic element.

11. The medical probe of claim 10, wherein the handle comprises a ratcheting mechanism configured to rotate so as to control amount of tension on at least one of the first puller wire and the second puller wire.

12. The medical probe of claim 1, further comprising a tube comprising a proximal end disposed within the elongated shaft and a distal end coupled to the PMA, the tube being configured to slide longitudinally in relation to the shaft to thereby change the length of the PMA.

13. The medical probe of claim 12, wherein the handle comprises a rocker configured to deflect the PMA from the longitudinal axis, and wherein a center of the rocker comprises an opening through which the tube passes.

14. A manufacturing method, comprising:
    affixing a probe maneuvering assembly (PMA) at a distal end of an elongated shaft such that the PMA and elongated shaft are aligned along a longitudinal axis;
    affixing a handle positioned at a proximal end of the elongated shaft;
    configuring the handle to change a length of the PMA;
    configuring the handle to deflect the PMA from the longitudinal axis; and
    positioning an expandable membrane around the PMA such that an internal volume of the expandable membrane changes in response to changing the length of the PMA and such that the expandable membrane deflects from the longitudinal axis in response to the PMA deflecting from the longitudinal axis.

15. The method of claim 14, further comprising:
    configuring the handle to change the length of the PMA independent of deflecting the PMA from the longitudinal axis.

16. The method of claim 14, further comprising:
    constructing the PMA to comprise a first elastic element configured to increase the internal volume of the expandable membrane by foreshortening the PMA and configured to decrease the internal volume of the expandable membrane by elongating the PMA; and constructing the PMA to comprise a second elastic element configured to deflect the PMA from the longitudinal axis, thereby deflecting the expandable membrane from the longitudinal axis.

17. The method of claim 16, further comprising:
surrounding at least a portion of the first elastic element by the second elastic element.

18. The method of claim 16, further comprising:
extending a first puller wire from the handle to the second elastic element; and
extending a second puller wire from the handle to the second elastic element.

19. A method, comprising:
inserting, into a cavity of an organ of a patient, a distal portion of a probe, the distal portion comprising an expandable membrane and a probe maneuvering assembly (PMA) disposed within the expandable membrane;
manipulating a proximal portion of the probe external to the patient, the proximal portion comprising a handle, and the probe comprising an elongated shaft extending from the handle to the PMA and defining a longitudinal axis of the probe;
manipulating the handle to thereby cause a change in length of the PMA and thereby a change in internal volume of the expandable membrane; and
manipulating the handle to thereby deflect the PMA from the longitudinal axis and thereby deflect the expandable membrane from the longitudinal axis.

20. The method of claim 19, further comprising:
manipulating the handle to thereby cause the change in length of the PMA independent of manipulating the handle to thereby deflect the PMA from the longitudinal axis.

* * * * *